United States Patent
Bhavsar et al.

(10) Patent No.: US 9,717,684 B2
(45) Date of Patent: Aug. 1, 2017

(54) STABLE MONTELUKAST SOLUTION

(71) Applicant: R.P. Scherer Technologies, LLC, Las Vegas, NV (US)

(72) Inventors: Krunal Bhavsar, Leicester (GB); Leon Paul Grother, Swindon (GB); Philip Axe, Abertridwr (GB)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 156 days.

(21) Appl. No.: 14/633,585

(22) Filed: Feb. 27, 2015

(65) Prior Publication Data

US 2015/0306031 A1 Oct. 29, 2015

Related U.S. Application Data

(60) Provisional application No. 61/984,098, filed on Apr. 25, 2014.

(51) Int. Cl.
| | | |
|---|---|---|
| *A61K 9/08* | (2006.01) | |
| *A61K 9/20* | (2006.01) | |
| *A61K 31/47* | (2006.01) | |
| *A61K 9/00* | (2006.01) | |
| *A61K 9/19* | (2006.01) | |

(52) U.S. Cl.
CPC .............. *A61K 9/08* (2013.01); *A61K 9/0056* (2013.01); *A61K 9/19* (2013.01); *A61K 9/20* (2013.01); *A61K 9/2063* (2013.01); *A61K 31/47* (2013.01)

(58) Field of Classification Search
None
See application file for complete search history.

(56) References Cited

U.S. PATENT DOCUMENTS

| | | | |
|---|---|---|---|
| 7,553,853 B2 | 6/2009 | Overeem et al. | |
| 2005/0187245 A1 | 8/2005 | Alnabari et al. | |
| 2006/0147482 A1* | 7/2006 | Chang ................. | A61K 9/0095 424/400 |
| 2007/0184101 A1 | 8/2007 | Hrakovsky et al. | |
| 2007/0208178 A1 | 9/2007 | Brand et al. | |
| 2008/0214823 A1* | 9/2008 | Padi ..................... | C07D 215/12 546/165 |
| 2009/0182148 A1 | 7/2009 | Chawla et al. | |
| 2011/0040095 A1* | 2/2011 | Bollikonda .......... | C07D 215/18 546/174 |

FOREIGN PATENT DOCUMENTS

| | | |
|---|---|---|
| EP | 2094664 A2 | 9/2009 |
| EP | 2094665 A2 | 9/2009 |
| WO | WO2005089761 A1 | 9/2005 |
| WO | WO2007005965 A1 | 1/2007 |
| WO | WO2008049922 A2 | 5/2008 |
| WO | WO2008058118 A2 | 5/2008 |
| WO | WO2010107404 A1 | 9/2010 |
| WO | WO2011120903 A2 | 10/2011 |
| WO | WO2012064301 A2 | 5/2012 |
| WO | WO2012064305 A2 | 5/2012 |
| WO | WO2012066401 A1 | 5/2012 |
| WO | WO2013037708 A1 | 3/2013 |
| WO | WO2013100701 A1 | 7/2013 |
| WO | WO2013103262 A1 | 7/2013 |

OTHER PUBLICATIONS

International Search Report and Written Opinion; Mailed Apr. 30, 2015 for the PCT Application No. PCT/US2015/017994.
Seager, H. "Drug-Delivery Products and the Zydis Fast-Dissolving Dosage Form," J. Pharm. Pharmacol. 1998. 50: 375-382.
Fu, Y., et al., "Orally Fast Disintegrating Tablets: Developments, Technologies, Taste-Masking and Clinical Studies," Critical Review in Therapeutic Drug Carrier Systems, 21(6): 433-475 (2004).
McLaughlin, R., et al., "ODTs Help Make the Medicine Go Down," Manufacturing Chemist, Nov. 2007, pp. 38-40.
Okumu, A., et al., "Dynamic Dissolution Testing to Establish In Vitro/In Vivo Correlations for Montelukast Sodium, a Poorly Soluble Drug," Pharmaceutical Research, 2008, vol. 25, No. 12, pp. 2778-2785.

* cited by examiner

*Primary Examiner* — Robert A Wax
*Assistant Examiner* — Quanglong Truong
(74) *Attorney, Agent, or Firm* — Mendelsohn Dunleavy, P.C.

(57) ABSTRACT

A solution that is stable at 5° C. to 30° C. for at least 24 hours, comprising: (a) water, (b) montelukast sodium; (c) a carrier material for a fast disintegrating dosage form; and (d) a component selected from a strong base, a bicarbonate salt and mixtures thereof. The solution comprising montelukast sodium is stable under conditions that are typically encountered during certain phases of the manufacturing process of fast disintegrating dosage form that contain the montelukast sodium. The solution can be used to form fast disintegrating dosage form tablets. A method of preparing a fast disintegrating dosage form tablet including preparing such solution, and forming a tablet, and a fast disintegrating dosage form that is prepared from the montelukast sodium solution are also described.

21 Claims, No Drawings

STABLE MONTELUKAST SOLUTION

FIELD OF THE INVENTION

The invention relates to a method of preparing a stable montelukast sodium solution for use in preparation of a fast-disintegrating dosage form.

DESCRIPTION OF THE RELATED TECHNOLOGY

The art of preparing solid dosage forms involves the preparation of a composition containing an active ingredient which is sufficiently sturdy for packaging and handling, and that disintegrates in a predictable manner.

Many patients find it difficult to swallow tablets and hard gelatin capsules and, as a result, do not take their medication as prescribed. It is estimated that 50% of the population is affected by this problem which results in a high incidence of non-compliance and ineffective therapy. The difficulty is experienced in particular by pediatric and geriatric patients, but it also applies to people who are ill in bed and to those active working patients who are busy or travelling.

Such problems have been addressed by various methods, including the development of a Zydis dosage form. See H. Seager, "Drug-Delivery Products and the Zydis Fast-dissolving Dosage Form", 50 *J. Pharm. Pharmacol.* 375-382 (1998). The Zydis fast dissolving dosage form is a unique freeze dried medicinal tablet. When Zydis units are put into the mouth, the freeze dried structure disintegrates instantaneously releasing the drug which dissolves or disperses in the saliva. The saliva containing the dissolved or dispersed medicament is then swallowed and the drug is absorbed.

The preparation of a fast disintegrating dosage form typically requires a solution hold period of up to 48 hours. Such a solution comprising montelukast sodium is susceptible to precipitation during this hold time. This precipitation is undesirable, as the solution components, including the active pharmaceutical ingredients and excipients, should be homogeneously dispersed in the composition throughout the manufacturing process in order to achieve uniform dosages in each fast disintegrating dosage form. The exact mechanism of precipitation is not certain, but it is believed to be due to montelukast sodium's propensity to form self-associated aggregates. See, for example, U.S. Pat. No. 7,553,853.

U.S. Pat. No. 7,553,853 teaches that montelukast sodium is not stable in aqueous solutions as precipitates may form after a certain period of time. Also, in such solutions, montelukast is surface active i.e., its behavior resembles a soap, which can cause problems in granulation processes for making tablets. These drawbacks are problematic to the montelukast manufacturing process. U.S. Pat. No. 7,553,853 sought to avoid this problem by using montelukast in solid form (a crystalline or amorphous solid) instead of montelukast sodium.

US 2006/0147482 discloses an oral liquid pharmaceutical formulation containing montelukast or its pharmaceutically acceptable salt in a buffer solution. The publication also teaches that addition of an organic solvent or an emulsifier to water will increase the solubility of montelukast in water. However, the publication found that montelukast or its salt is not stable in a solution containing both water and an organic solvent, even though the solubility of the montelukast sodium in the solution is increased by addition of the organic solvent. This publication suggests the addition of a buffering agent to the montelukast sodium solution containing both water and an organic solvent. The buffering agent may be phosphoric acid/hydroxide, phosphate salt/hydroxide, boric acid/potassium chloride/hydroxide, tetraborate/inorganic acid, tetraborate/hydroxide or carbonate/bicarbonate.

WO 2013/037708 discloses a fast dissolving pharmaceutical formulation containing an open matrix network carrying a pharmaceutically active ingredient. The pharmaceutical composition may contain a pH adjusting agent to adjust the pH of a solution from which the fast dissolving formulation is prepared.

WO 2012/064305 discloses a tablet formulation including a combination of montelukast and levocetirizine. This bilayer tablet formulation is prone to degrade easily. The bilayer tablet formulation comprises pharmaceutically suitable additives and excipients such as stabilizing agents. Such stabilizing agents may be used to increase stability of montelukast in the tablets and such agents may include sodium hydrogen carbonate or sodium hydroxide, among a long list of stabilizing agents.

WO 2008/049922 discloses a process for preparing montelukast acid or its pharmaceutically acceptable salts. The process involves multiple chemical reactions. A base may be used for at least one of these chemical reactions. The publication lists film coated tablets as one of several formulations in which montelukast sodium may be used.

Okumu et al., "Dynamic dissolution testing to establish in vitro/in vivo correlations for montelukast sodium, a poorly soluble drug," 25 *Pharm Res., pp.* 2778-2785 (2008) discloses that montelukast sodium has low solubility in water at low pH and that the solubility increases with increasing pH. Therefore, it is expected that adjusting the pH of an aqueous solution of montelukast sodium will affect the solubility of montelukast sodium in the aqueous solution but this reference does not determine whether pH affects the stability of the montelukast sodium solution, once the montelukast has been dissolved.

Accordingly, there is need to provide for a solution comprising montelukast sodium and components of a fast disintegrating dosage form that is stable in a dissolved state for at least 24 or 48 hours.

SUMMARY OF THE INVENTION

In general terms, the present invention is directed to a solution that is stable at about 5° C. to about 30° C. for at least 24 or 48 hours comprising: water, montelukast sodium, at least one matrix-forming component of a fast disintegrating dosage form; and a least one component selected from a strong base, a bicarbonate and mixtures thereof.

The solution comprising montelukast sodium is designed to be stable at about 5° C. to about 30° C. for at least 24 or 48 hours under conditions that are typically encountered during certain phases of the process of manufacturing fast disintegrating dosage forms that contain the montelukast sodium. For example, the solution is stable at temperatures that may be encountered, for example, during a hold period used in the process of manufacturing fast disintegrating dosage form tablets containing montelukast sodium.

The solution of the present invention may be a homogeneous aqueous solution that can be readily used to form fast disintegrating dosage form tablets.

Further, the present invention is also directed to a method of preparing a fast disintegrating dosage form tablet comprising a step of preparing a solution that is stable at about 5° C. to about 30° C. for at least 24 or 48 hours, comprising: (a) water; (b) montelukast sodium; (c) at least one matrix-forming component of a fast disintegrating dosage form; and (d) at least one component selected from a strong base, a bicarbonate and mixtures thereof.

Also, the present invention is directed to a fast disintegrating dosage form that is prepared from the stable solution containing montelukast sodium as described above.

DETAILED DESCRIPTION

For illustrative purposes, the principles of the present disclosure are described by referencing various exemplary embodiments. Although certain embodiments are specifically described herein, one of ordinary skill in the art will readily recognize that the same principles are equally applicable to, and can be employed in other devices and methods. Before explaining the disclosed embodiments of the present disclosure in detail, it is to be understood that the disclosure is not limited in its application to the details of any particular embodiment shown. Additionally, the terminology used herein is for the purpose of description and not of limitation. The definition of a phrase or a term may include several examples. Such examples are not an exhaustive definition of the phrase of term to be defined.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

The present invention is directed to a solution stable at room temperature comprising: (a) water; (b) montelukast sodium; (c) a matrix-forming agent for a fast disintegrating dosage form; and (d) at least one component selected from a strong base, a bicarbonate and mixtures thereof.

The solution comprising montelukast sodium is designed to be stable under conditions, such as temperature, that are typically encountered during certain phases of the process of manufacturing fast disintegrating dosage forms that contain the montelukast sodium. In one embodiment, the solution of the present invention is stable for at least 24 hours at a temperature between about 5° C. and about 30° C. In another embodiment the solution is stable for at least 48 hours at a temperature between about 5° C. and about 30° C. In still another embodiment of the present invention the solution is stable for at least 72 hours at a temperature between about 5° C. and about 30° C.

In another embodiment, the solution of the present invention is stable for 24, 48 or 72 hours at a temperature between about 20° C. and about 26° C. In yet another embodiment the solution of the present invention is stable for 24, 48 or 72 hours at about 23° C.

The solution of the present invention may be a homogeneous aqueous solution that can be readily used to form fast disintegrating dosage form tablets. Such a solution generally appears as clear. The solution is typically made from a combination of a dry powder and an aqueous component, and thus various components of the composition may be added to the dry powder, aqueous component or a preformed aqueous composition made by mixing the dry powder and the aqueous component.

The term "stable" as used herein, refers to a solution that is not substantially altered or altered when subjected to conditions of production, detection, and, in certain aspects, recovery, purification, and use for one or more of the purposes disclosed herein. The term "stable" also means that the solution does not separate or form a precipitate. The stability of the solution is to be determined by the test method set forth in the examples given below.

The solvent used in forming the solution of the pharmaceutically active substance is water. In one embodiment of the present invention the solution does not comprise any solvent other than water. One of the advantages of such embodiment of the present invention is that no co-solvents (such as alcohols or organic solvents) are required to form a stable solution that is stable at a temperature between about 5° C. and about 30° C.

The solution of the present invention comprises the active pharmaceutical ingredient montelukast sodium. The solution also comprises one or more matrix-forming components of a fast disintegrating dosage form. The amount of pharmaceutically active substance contained within each unit dosage will depend upon the drug characteristics but may be up to about 20 mg per unit dosage, preferably, 4 mg, 5 mg or 10 mg per unit dosage. The Montelukast sodium can be used at levels of up to about 10% by weight of the solution, up to about 5% by weight or up to about 3% by weight in the solution used in the preparation of the unit dosages in accordance with the process of the invention.

Montelukast sodium is a sodium salt form of montelukast. Montelukast is a leukotriene receptor antagonist used for the maintenance treatment of asthma and to relieve symptoms of seasonal allergies. In its pure state, montelukast is (R,E)-2-(1-((1-(3-(2-(7-chloroquinolin-2-yl)vinyl)phenyl)-3-(2-(2-hydroxypropan-2-yl)phenyl)propylthio)methyl)cyclopropyl)acetic acid. Alternatively, montelukast is [R-(E)]-1-[[[1-[3-[2-(7-chloro-2-quinolinyl)ethenyl]phenyl]-3-[2-(1-hydroxy-1-methylethyl)phenyl]propyl]thio]methyl] cyclopropaneacetic acid.

One component of the fast disintegrating dosage form of the invention is a carrier material for a fast disintegrating solid dosage form. The carrier material forms a network or matrix containing the pharmaceutically active substance. The carrier material may be any water-soluble or water-dispersible material that is pharmaceutically acceptable, inert to the pharmaceutically active substance and which is capable of forming a rapidly disintegrating network. In carrying out the process of the present invention the carrier is generally incorporated into the solution in an amount of from 1 to 6% by weight, preferably in an amount of from 1.5 to 4% by weight, based on the total weight of the solution.

Exemplary carrier materials include gelatins, alginates, hydroxyethyl cellulose, sodium carboxymethyl cellulose, microcrystalline cellulose, corn-syrup solids, pectin, carrageenan, agar, chitosan, locust bean gum, xanthan gum, guar gum, acacia gum, tragacanth, konjac flour, rice flour, wheat gluten, sodium starch glycolate, soy fiber protein, potato protein, papain, horseradish peroxidase, poly(vinyl alcohol), polyvinylpyrrolidone, pullulan, modified starch and mixtures thereof. Mixtures of two or more of the carrier materials may be used in the solution.

In one embodiment of the present invention the carrier material comprises polymer component. One preferred polymer component is a gelatin, such as plain gelatin, partially hydrolyzed gelatin and pharmaceutical grade gelatin. The gelatins used in the present invention may include type A gelatin, with an isoionic point of 7 to 9, type B gelatin, with an isoionic point of 4.8 to 5.2 and mixtures thereof. Another preferred polymer component is pullulan (i.e., a polysaccharide polymer consisting of maltotriose units). Yet another preferred polymer component is modified starch.

In a preferred embodiment, the carrier material of the present invention is combined with a filler or bulking agent. The filler or bulking agent is generally incorporated into the solution in an amount of from 1 to 6% by weight, preferably in an amount of from 1.5 to 4% by weight, based on the total weight of the solution. The filler or bulking agent usually present in the fast disintegrating dosage form is a saccharide, and may be a monosaccharide, disaccharide, or a polysaccharide. Examples of suitable saccharides include dextrose such as hydrolyzed dextrose, dextran, dextrin, maltodextrin, sorbitol, mannitol, xylitol, saccharose, glucose, lactose and fructose. In one embodiment of the present invention the saccharide is mannitol. More than one such saccharide may be used in the solution. In one preferred embodiment of the present invention the saccharide is mannitol. In specific embodiments, the carrier material may contain a combination of gelatin and a saccharide such as mannitol.

In one embodiment of the invention, the carrier material is a polymer and the solution also contains a saccharide. In another embodiment, the carrier material is gelatin and the solution also includes a saccharide.

The solution of the present invention also includes a component which aides in maintaining the homogeneity of the composition, and prevents separation of the ingredients of the solution. This component may be a solubility enhancer. In one embodiment, the solubility enhancer helps to maintain all of the ingredients of the solution in a solution.

The component which aides in maintaining the homogeneity of the solution may be a strong base, bicarbonate or a mixture thereof. Examples of strong bases include alkali metal hydroxides and alkaline earth metal hydroxides and mixtures thereof. Examples of alkali metal hydroxides include sodium hydroxide, potassium hydroxide and mixtures thereof. One example of an alkaline earth metal hydroxide is magnesium hydroxide. The strong base may be added to the solution to adjust the pH to a pH greater than 9.0. Alternatively, the strong base may be added to the solution to adjust the pH to a pH greater than 9.5. One preferred strong base is sodium hydroxide which may be used in combination with a carrier material comprising gelatin and a saccharide such as mannitol.

The bicarbonate may be provided to the solution, for example, as a bicarbonate salt formed by a combination of bicarbonate and a cation. The cation is selected such that the bicarbonate salt with the cation is soluble in the solution. Examples of suitable bicarbonates include alkali metal bicarbonates, alkaline earth metal bicarbonates, and ammonium bicarbonate. Only those alkaline earth metal bicarbonates having a solubility sufficient to form a homogenous solution including sufficient bicarbonate to improve the stability of the solution may be employed. One preferred bicarbonate salt is sodium bicarbonate which may be used in combination with a carrier material comprising gelatin and a saccharide such as mannitol.

In one embodiment of the present invention, the component which aides in maintaining the homogeneity of the solution or solubility enhancer has a higher molarity in the composition than the montelukast sodium. In this embodiment, the molar ratio of the montelukast sodium to the component which aides in maintaining the homogeneity of the solution or the solubility enhancer is between about 0.5:1 and about 10:1, or between about 0.75:1 and about 6:1.

In addition to the foregoing components, the solution of the present invention may comprise additional ingredients such as, for example, structure builders, matrix formers, structure formers, structure promotors, flow aids, bulking agents, disintegrants, preservatives, binding agents, stabilizers, emulsifiers, solubilizers, sweeteners, flavors, pH modifiers, colors, fillers, and osmotic pressure regulators.

Structure builders are compounds which provide the required shape and tensile strength of the product. Examples of structure builders include sugar alcohols such as mannitol or xylitol, sugars such as saccharose, glucose, lactose, and fructose and mixtures thereof.

Examples of other ingredients that may be used include sugar alcohols, sugars, cellulose powder, dicalcium phosphate, calcium sulfate, microcrystalline cellulose, glycine, starches, aroma compounds, dyestuffs and pigments, solid buffers and similar compounds.

Binders with suitable binding ability and properties supporting formation of a sturdy structure of the lyophilisate, e.g. gelatin, povidone, soluble cellulose ether and the like. Suitable binders may be selected from tablet binding agents which show good binding properties and also support the structural stability of the lyophilisate, for example hydrolysed or non-hydrolysed gelatin, polyvinylpyrrolidone, cellulose ether, pre-gelatinized starch and the like.

A bulking agent provides bulk and structure to the lyophilization cake. The bulking agent is inert. In addition, the bulking agent is capable of crystallizing under lyophilization conditions. Examples of suitable bulking agents include hydrophilic components, such as, water soluble polymers; sugars, such as mannitol, sorbitol, xylitol, glucitol, dulcitol, galactitol, inositol, arabinitol, arabitol, galactitol, iditol, allitol, maltitol, fructose, sorbose, glucose, xylose, trehalose, allose, dextrose, altrose, lactose, gulose, idose, galactose, talose, ribose, arabinose, xylose, lyxose, sucrose, maltose, lactulose, fucose, rhamnose, melezitose, maltotriose, raffinose, altritol, their optically active forms (D- or L-forms) as well as the corresponding racemates; inorganic salts, both mineral and mineral organic, such as, calcium salts, such as the lactate, gluconate, glycerylphosphate, citrate, phosphate monobasic and dibasic, succinate, sulfate and tartrate, as well as the same salts of aluminum and magnesium; carbohydrates, such as, the conventional mono- and di-saccharides as well as the corresponding polyhydric alcohols; proteins, such as, albumin; amino acids, such as glycine; emulsifiable fats, polyvinylpyrrolidone, sodium chloride, starch, hydroxyethylstarch (hetastarch), cellulose, cyclodextrins, glycine, and mixtures thereof.

Flavors may optionally be added to either the dry powder or the aqueous liquid or both to mask bitterness or to match marketing requirements.

Sweeteners may optionally be added to either the dry powder or the aqueous liquid or both. Exemplary sweeteners include high intensity sweeteners, such as aspartame, acesulfame K, sucralose, and like.

The amount of the components in the solution of the present invention is generally guided by desired amounts of the components present in the fast disintegrating dosage form prepared by using the solution of the present invention. For example, the carrier material for a fast disintegrating dosage form may be between 1 and 20 wt % of the solution, or between 1 and 10 wt % of the solution or between 1 and 6 wt % of the solution. Similarly, the saccharide may be present in the fast disintegrating dosage form at 1 to 20 wt % of the solution, or between 1 and 10 wt % of the solution or between 1 and 6 wt % of the solution. The weight ratio of montelukast sodium to the saccharide may be in the range of 1:0.2 to 1:10.

The present invention is also directed to a method of preparing a fast disintegrating dosage form such as a tablet, comprising a step of preparing an solution that is stable at about 5° C. to about 30° C. for at least 24, 48 or 72 hours. The solution includes: (a) water; (b) montelukast sodium; (c)

one or more carrier materials of a fast disintegrating dosage form; and (d) at least one component which aides in maintaining the homogeneity of the solution selected from a strong base, bicarbonate and mixtures thereof.

The solution prepared according to the process of the present invention is preferably formed into discrete units by introduction into a mould which preferably comprises a plurality of depressions, each depression being of the desired shape and size for the oral dosage form product. The mould preferably comprises a plurality of depressions formed in a sheet of a filmic material which may be similar to the material employed conventionally in the blister packaging of pharmaceuticals. A filmic material for use as a mould in the present invention is described in WO94/12142. The desired quantities of the solution may be filled into the mould using an automatic filling means which delivers a predetermined dose into each of the depressions in the mould.

A covering material may be adhered to the filmic material in the area surrounding the depressions after the removal of solvent from solution filling the depressions. The covering sheet is preferably an aluminum foil or aluminum foil laminate which may be adhered to the filmic material around the depressions by, for example a heat sensitive material. The cover sheet may be adhered to the filmic material in a manner such that it can be peeled away by the user to uncover the oral dosage form in the depression in the mould or, alternatively, it may be adapted for the oral dosage forms to be pushed through.

The removal of water from the discrete units of the solution comprising the pharmaceutically active substance is carried out by techniques well known to those skilled in the art. When the discrete units are in liquid form they will generally be frozen or gelled prior to drying.

The solution which may be contained within the pockets of a suitable mould is frozen, for example by passing a gaseous cooling medium, such as liquid nitrogen over the mould, or by inserting the mould into a nitrogen spray freezing chamber, or cooling by passing the mould over a cold surface. Once the dosage forms have been frozen, the mould may be stored in a cold store, prior to drying. Frozen discrete units may be dried by freeze drying according to techniques which are well known in the art. The solvent is sublimed in a freeze drying process under a reduced pressure which transforms the solid solvent directly into a vapor. The freeze drying process will generally be carried out in a freeze drying chamber typically operating under a vacuum of 0.1 to 1.0 mbar for a period of time from 180 to 500 minutes.

The present invention is also directed to a fast disintegrating dosage form tablet that is prepared from a stable montelukast sodium composition. The fast disintegrating dosage form tablet may be prepared by preparing an solution that is stable at about 5° C. to about 30° C. for at least 24, 48 or 72 hours, comprising: (a) water, (b) montelukast sodium; (c) at least one carrier material of a fast disintegrating dosage form; and (c) at least one component which aides in maintaining the homogeneity of the solution selected from a strong base, bicarbonate and mixtures thereof.

The phrase "fast disintegrating dosage form", or FDDF, refers to a dosage form capable of delivering an active ingredient in a solid dosage form which upon exposure to water rapidly disintegrates. The terms "disintegration", the adjective form thereof, such as "disintegrating", and the verb form thereof, such as "to disintegrate", are related to the physical reaction of the dosage form in water, or an aqueous solution, or a fluid such as may be found on a mucous membrane. The disintegration of the dosage form means that the structure of the dosage form breaks down from solid, or solid-like, to form a heterogeneous mixture, solution, suspension or colloid. Because of the differences in the properties of the components of the dosage form, formation of a solution, suspension, colloid, or a heterogeneous composition occurs after disintegration.

An example of a fast disintegrating dosage form is a solid dosage form that disintegrates on the tongue, to aid in oral administration of an active pharmaceutical ingredient. Another example of a fast dissolving dosage form is a mouth dissolving tablet, also known as an MDT. Another example of a fast dissolving dosage form is an orally disintegrating tablet, also known as ODT. An orally disintegrating tablet is a solid dosage form containing medicinal substances which disintegrates rapidly, usually within a matter of seconds, when placed upon the tongue.

In one embodiment of the present invention, the fast dissolving dosage form is an orally disintegrating tablet that weighs less than 500 mg. The orally disintegrating tablet of the present invention may disintegrate in less than 30 seconds, as determined by an in vitro disintegration test. An example of such a disintegration test is the United States Pharmacopeia, ⟨701⟩ Disintegration.

Another example of a fast dissolving dosage form is an orodispersible tablet. An orodispersible tablet is an uncoated tablet intended to be placed in the mouth where it disperses rapidly before being swallowed. In one embodiment of the present invention, the fast dissolving dosage form is an orodispersible tablet that disintegrates within 3 minutes when subjected to the disintegration test mentioned above.

Examples

The invention is further described in the following examples, which are not intended to limit the scope of the invention as claimed.

Gelatin EP/USNF/JP (Deutsche Gelatine-Fabriken Stoess AG), mannitol EP/USP, and montelukast sodium were dissolved in water, in the amounts indicated in Table 1. The pH of the resulting composition was measured. Buffering agent was then added, and the pH was measured again. Each composition was shaken until a clear homogeneous solution was achieved. The six compositions were left to stir at 22° C. for 48 hours. The visual appearance of each of the compositions, as determined immediately after mixing of the solutions, after 24 hours and after 48 hours are given in Table 1.

TABLE 1

| | Examples 1 to 6 | | | | | |
|---|---|---|---|---|---|---|
| | 1 | 2 | 3 | 4 | 5 | 6 |
| | Material (% w/w) | | | | | |
| Gelatin EP/USNF/JP | 4.00 | 4.00 | 4.00 | 4.00 | 4.00 | 4.00 |
| Mannitol EP/USP | 3.00 | 3.00 | 3.00 | 3.00 | 3.00 | 3.00 |

TABLE 1-continued

Examples 1 to 6

|  | 1 | 2 | 3 | 4 | 5 | 6 |
|---|---|---|---|---|---|---|
| Montelukast Na | 2.77 | 2.77 | 2.77 | 2.77 | 2.77 | 2.77 |
| Purified water | 89.82 | 89.67 | 89.91 | 89.76 | 89.38 | 89.08 |
| Buffering agent | | | | | | |
| Buffering agent $pK_b$ | 11.84 | 7.7 | 9.25 | 7.63 | 7.7 | — |
| Dibasic sodium phosphate | 0.41 | | | | | |
| Potassium citrate | | 0.56 | | | | |
| Sodium acetate | | | 0.32 | | | |
| Sodium bicarbonate | | | | 0.47 | | |
| Sodium citrate dihydrate | | | | | 0.85 | |
| Sodium hydroxide (3% w/w) | | | | | | 1.15 |
| Total | 100.00 | 100.00 | 100.00 | 100.00 | 100.00 | 100.00 |
| Montelukast Na:Buffering agent molar ratio | 1.57:1 | 2.49:1 | 1.17:1 | 0.81:1 | 1.57:1 | 5.29:1 |
| pH before addition of a buffering agent | 8.59 | 8.61 | 8.60 | 8.61 | 8.62 | 8.67 |
| pH after addition of a buffering agent | 8.60 | 8.35 | 8.57 | 8.46 | 8.52 | 9.79 |
| Visual appearance | | | | | | |
| Initial | Clear, yellow | Clear, yellow | Clear, yellow | Clear, yellow | Clear, yellow | Clear, pale yellow |
| 24 hours | Cloudy, yellow | Cloudy, yellow | Cloudy, yellow | Clear, yellow | Cloudy, yellow | Clear, pale yellow |
| 48 hours | Off-white suspension | Off-white suspension | Off-white suspension | Clear, yellow | Off-white suspension | Clear, pale yellow |

During the addition of the buffering agent it was noted that the pH values for each of the compositions stayed about the same or decreased by a small amount. The exception was the composition with sodium hydroxide, where the pH increased by about one unit.

Each of the compositions with dibasic sodium phosphate, potassium citrate, sodium acetate, sodium bicarbonate, sodium citrate dihydrate, and sodium hydroxide were clear upon mixing. In each case the composition was yellowish or pale yellow. After 24 hours, the compositions with dibasic sodium phosphate, potassium citrate, sodium acetate, and sodium citrate dihydrate were cloudy, whereas the compositions with sodium bicarbonate and sodium hydroxide continued to be clear. After an additional 24 hours, the compositions with dibasic sodium phosphate, potassium citrate, sodium acetate, and sodium citrate dihydrate were an off-white suspension, whereas the compositions with sodium bicarbonate and sodium hydroxide continued to be clear. After another 24 hours (a total of 72 hours), the composition containing sodium hydroxide began to show signs of slight cloudiness.

Fast disintegrating dosage form tablets comprising 5.00 mg of montelukast were prepared based on the formulations of Examples 4 and 6. Two batches of tablets for each of the two formulations were tested for stability using accelerated stability conditions at a constant temperature of 60° C. for 12 weeks.

The assay results for both formulations show mean assay values of montelukast of about 4.91 to 4.99 mg/tablet. These results show that the fast disintegrating dosage form tablets are stable at a constant temperature of 60° C. for 12 weeks, which indicates that such tablets should be sufficiently stable to meet regulatory stability requirements with respect to the active pharmaceutical ingredient.

The stability of the montelukast sodium comprising sodium hydroxide compared favorably with commercially available montelukast sodium marketed as Singulair 5 mg montelukast. The stability data at 25° C./60% RH for 5 mg tablets of Singulair is contrasted with fast disintegrating dosage form tablets comprising montelukast sodium and sodium hydroxide in Table 2. The stability data at 40° C./75% RH for 5 mg tablets of Singulair is contrasted with fast disintegrating dosage form tablets comprising montelukast sodium and sodium hydroxide in Table 3.

TABLE 2

Stability data at 25° C./60% RH for 6 months

|  | Months | | | | |
|---|---|---|---|---|---|
|  | Initial | 1 | 2 | 3 | 6 |
| Singulair 5 mg tablet | | | | | |
| Montelukast (mg/tab) | 5.05 | 5.07 | 5.13 | 5.10 | 5.04 |
| Sulfoxide impurity (%) | 0.47 | 0.51 | 0.52 | 0.56 | 0.61 |
| Total impurity (%) | 2.29 | 2.02 | 2.21 | 2.14 | 2.27 |
| FDDF montelukast sodium | | | | | |
| Montelukast (mg/tab) | 5.08 | 5.06 | 5.09 | 5.12 | 5.09 |
| Sulfoxide impurity (%) | 0.13 | 0.18 | 0.17 | 0.16 | 0.18 |
| Total impurity (%) | 0.81 | 0.63 | 0.80 | 0.65 | 0.73 |

TABLE 3

Stability data at 40° C./75% RH for 6 months

|  | Months | | | | |
|---|---|---|---|---|---|
|  | Initial | 1 | 2 | 3 | 6 |
| Singulair 5 mg tablet | | | | | |
| Montelukast (mg/tab) | 5.05 | 5.09 | 5.03 | 5.04 | 5.01 |
| Sulfoxide impurity (%) | 0.47 | 0.67 | 0.82 | 0.97 | 1.34 |
| Total impurity (%) | 2.29 | 2.10 | 2.51 | 2.49 | 2.95 |

TABLE 3-continued

Stability data at 40° C./75% RH for 6 months

| | Months | | | | |
|---|---|---|---|---|---|
| | Initial | 1 | 2 | 3 | 6 |
| FDDF montelukast sodium | | | | | |
| Montelukast (mg/tab) | 5.08 | 5.07 | 5.04 | 5.08 | 5.02 |
| Sulfoxide impurity (%) | 0.13 | 0.25 | 0.53 | 0.49 | 0.69 |
| Total impurity (%) | 0.81 | 0.73 | 1.15 | 1.06 | 1.41 |

The stability results at 25° C./60% RH and 40° C./75% RH demonstrated better stability for the montelukast sodium fast disintegrating dosage form comprising montelukast sodium and sodium hydroxide than the currently marketed product Singulair 5 mg montelukast. The montelukast sodium fast disintegrating dosage form comprising montelukast sodium and sodium hydroxide exhibited a significant reduction in the amount of the main impurity sulfoxide as well as approximately a 55% to 70% reduction in the amount of total impurities compared to the tested Singulair 5 mg montelukast formulation.

The montelukast sodium formulation with sodium bicarbonate demonstrated improved stability compared to the montelukast sodium formulation with sodium hydroxide at accelerated stability conditions of 60° C. for 4 weeks. Based on these results the montelukast sodium fast disintegrating dosage form tablets with sodium bicarbonate are likely to have improved long term stability compared with the montelukast sodium fast disintegrating dosage form tablet 5 mg formulation with sodium hydroxide and thus would therefore be expected to show a significant improvement in stability over the currently marketed product Singulair 5 mg montelukast.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A solution that is stable at a temperature between about 5° C. to about 30° C. for at least 24 hours, comprising:
   (a) water;
   (b) montelukast sodium;
   (c) a carrier material for a fast disintegrating dosage form; and
   (d) a component selected from a strong base, a bicarbonate salt and mixtures thereof, wherein the solution does not contain any solvent other than water.

2. The solution of claim 1, further comprising:
   (e) a saccharide.

3. The solution of claim 2, wherein component (e) comprises mannitol.

4. The solution of claim 2, wherein component (e) is mannitol.

5. The solution of claim 1, wherein the molar ratio of component (b) to component (d) is from about 0.5:1 to about 10:1.

6. The solution of claim 1, wherein the molar ratio of component (b) to component (d) is from about 0.75:1 to about 6:1.

7. The solution of claim 1, wherein the component (d) is a strong base selected from an alkali metal hydroxides and alkaline earth metal hydroxides and mixtures thereof.

8. The solution of claim 7, wherein the component (d) is sodium hydroxide.

9. The solution of claim 1, having a pH of at least 9.0.

10. The solution of claim 1, having a pH of at least 9.5.

11. The solution of claim 1, wherein the component (d) is a bicarbonate salt selected from alkali metal bicarbonates, alkaline earth metal bicarbonates, ammonium bicarbonate and mixtures thereof.

12. The solution of claim 11, wherein component (d) is sodium bicarbonate.

13. The solution of claim 1, wherein the component (c) is selected from gelatins, alginates, hydroxyethyl cellulose, sodium carboxymethyl cellulose, microcrystalline cellulose, corn-syrup solids, pectin, carrageenan, agar, chitosan, locust bean gum, xanthan gum, guar gum, acacia gum, tragacanth, konjac flour, rice flour, wheat gluten, sodium starch glycolate, pullulan, modified starch, soy fiber protein, potato protein, papain, horseradish peroxidase, poly(vinyl alcohol), polyvinylpyrrolidone, and mixtures thereof.

14. The solution of claim 13, wherein the component (c) comprises gelatin.

15. The solution of claim 13, wherein the component (c) is gelatin.

16. The solution of claim 2, wherein components (c) and (e) are each present in an amount of 1-6 wt %, based on the total weight of the solution.

17. The solution of claim 1, that is stable at a temperature between about 5° C. to about 30° C. for at least 24 hours.

18. The solution of claim 1, that is stable at a temperature between about 5° C. to about 30° C. for at least 48 hours.

19. A method of preparing a fast disintegrating dosage form tablet comprising steps of:
   preparing the solution as claimed in claim 1, and
   forming a tablet from said solution.

20. The method of claim 19, wherein said step of forming a tablet comprises lyophilization.

21. A fast disintegrating dosage form tablet prepared by the method of claim 19.

* * * * *